United States Patent [19]

Lindholm

[11] Patent Number: 6,102,981

[45] Date of Patent: Aug. 15, 2000

[54] METHOD FOR CONTROLLING THE COMPOSITION OF A CAST IRON MELT

[75] Inventor: Ragnar Lindholm, Bromma, Sweden

[73] Assignee: SinterCast AB, Stockholm, Sweden

[21] Appl. No.: 09/155,016

[22] PCT Filed: Feb. 28, 1997

[86] PCT No.: PCT/SE97/00350

§ 371 Date: Sep. 16, 1998

§ 102(e) Date: Sep. 16, 1998

[87] PCT Pub. No.: WO97/35184

PCT Pub. Date: Sep. 25, 1997

[30] Foreign Application Priority Data

Mar. 18, 1996 [SE] Sweden .................................. 9601026

[51] Int. Cl.[7] .................................................. C22C 33/08
[52] U.S. Cl. ............................ 75/382; 136/231; 164/4.1; 266/79; 420/18
[58] Field of Search .............................. 75/382; 164/4.1; 136/231; 266/79; 420/18

[56] References Cited

U.S. PATENT DOCUMENTS 5,949,000  7/1999  Lindholm et al. .................... 73/864.91

FOREIGN PATENT DOCUMENTS

91/13176  9/1991  WIPO .
92/06810  4/1992  WIPO .
92/06809  4/1999  WIPO .

*Primary Examiner*—Melvyn Andrews
*Attorney, Agent, or Firm*—Pillsbury Madison & Sutro LLP

[57] ABSTRACT

A method for controlling the composition of a cast iron melt is presented. A cast iron melt is prepared which has added to it a structure modifying agent and a nucleating agent in amounts selected to produce a fully compacted graphite iron upon solidification of the melt. A sample vessel, having an inner wall having an active portion coated with a material which will lower the concentration of dissolved modifying agent and an inert portion, is used to extract a sample of the melt. Three temperature measuring devices are used to measure temperatures at three locations within the melt. One measuring device measures the temperature at the center of the vessel, one measures the temperature at the inert portion of the vessel's inner surface and one measures the temperature at the active portion of the vessel's inner surface. In another aspect of the invention, two sample vessels are used, one having an active surface and the other having an inert surface.

14 Claims, 3 Drawing Sheets

METHOD FOR CONTROLLING THE COMPOSITION OF A CAST IRON MELT

This application is a national phase of international application PCT/SE97/00350 filed Feb. 28, 1997 which designated the U.S.

In the foundry industry it is often desirable to be able to determine in which matrix structure a certain molten cast iron will solidify. One way of carrying out such determinations is to perform a thermal analysis of the melt. A small sample of the molten metal alloy is taken and is allowed to solidify. During this process, the temperature is measured as a function of time. The configuration is then determined by comparing the obtained cooling curve and its time derivative with reference curves. Such thermal analysis methods are disclosed in e.g. WO86/01755, WO91/13176 and WO92/06809.

In the above mentioned methods, a sample of molten metal is obtained by immersing a sample vessel into the molten iron, whereafter said sample is allowed to solidify. The thermal analysis is performed by using temperature responsive means, normally two thermocouples. One of said means is positioned in the centre of the vessel and the other near the vessel wall.

In the method according to WO92/06809 a sample vessel where the inner surface is coated with a reactive wall is used. The reactive coating, comprising oxides of silicon, manganese, iron and/or sodium, reacts with active magnesium in the sampled iron and lowers the level of active magnesium in the wall region of the sample vessel.

By using a coated sample vessel according to WO92/06809 it is possible to perform more accurate predictions of solidification structure compared to the state of the art as represented by WO86/01755. In particular, the consumption of magnesium in the near-wall region simulates the natural fading of magnesium during the casting period and provides a predictive warning of magnesium loss. While this feature is indespensible for for the reliable production of compacted graphite iron, it is of great importance to be able to increase the accuracy further.

SUMMARY OF THE INVENTION

Now it has turned out that by using at least three temperature responsive means instead of two and by using a sample vessel where a part of the inner surface is coated with a layer of a substance which will lower the concentration of dissolved elementary magnesium, and the rest of the inner surface is coated by an inert or non-reactive substance (oxides-of alumina and zirconia for example), or the sample vessel itself is non-reactive (quartz or steel), it is possible to further increase the accuracy of the solidification structure predictions of the molten cast iron. Alternatively, two different sample vessels, one being coated with a reactive layer and the other one being essentially inert or non-reactive, or coated with an inert or non-reactive substance, may also be used in the present method. Suitable temperature responsive means are thermocouples or pyrometrical means.

A sample of the molten cast iron that is to be analyzed is taken and poured into said sample vessel, which is partially coated with reactive and non-reactive coatings. At least one of the temperature responsive means is placed in the centre of the sample vessel, at least one means close to the inner surface to which a reactive coating has been applied, and at least one means close to the inner surface, to which a non-reactive coating has been applied. Each of said temperature responsive means is then used to record the temperature of the melt during the solidification process as a function of time. The obtained curves are then evaluated in order to determine the configuration of the solidified cast iron sample.

DETAILED DESCRIPTION OF THE PRESENT INVENTION

The present invention will be explained in more detail with reference to the figures, in which FIG. 1 shows typical cooling curves that can be obtained by using the method according to WO86/01755;

FIG. 2 illustrates a diagram showing the nodularity percentage as a function of the magnesium percentage. In this diagram 0% nodularity corresponds to a complete compacted graphite cast iron (CGI), whereas 100% corresponds to a complete spheroidal graphite iron (SGI); Finally, values below 0% nodularity relate to grey cast iron. Actually, 0% nodularity corresponds to 100% compacted graphite cast iron and the bottom of this axis corresponds to 100% flaky grey cast iron;

Figure 1:
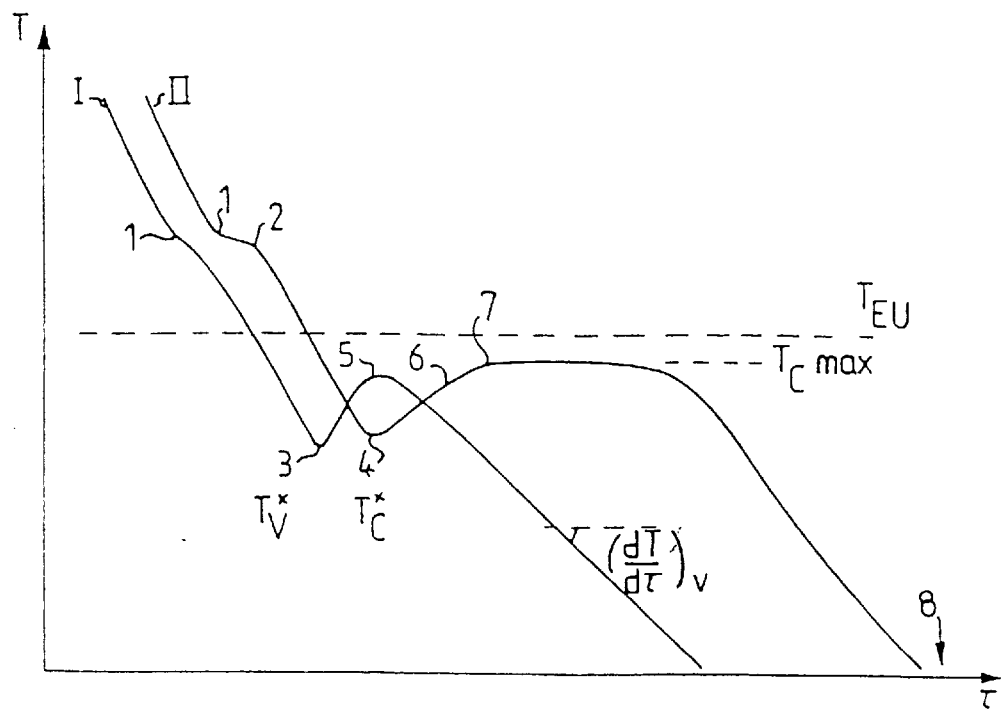

As previously mentioned, the procedure for predicting in which matrix structure a molten cast iron will solidify according to WO86/01755 makes use of two thermocouples, one arranged in the center of the sample vessel and the other near the vessel wall. These two thermocouples provide two distictly different cooling curves which are illustrated in FIG. 1.

The description of key points on these curves is properly made in WO86/01755. A second consideration to be made during the interpretation of the cooling curves is taught in WO92/06809. In this case, a reactive coating on the sample wall consumes magnesium from the melt and causes the near-wall region to solidify as grey iron. The latent heat liberated by the precipitation and growth of grey iron graphite flakes causes a "deflection" in the normal wall cooling curve. The grey iron/compacted graphite iron (CGI) transition and the "deflected" wall curve are illustrated in FIGS. 2 and 3 respectively.

Figure 2:
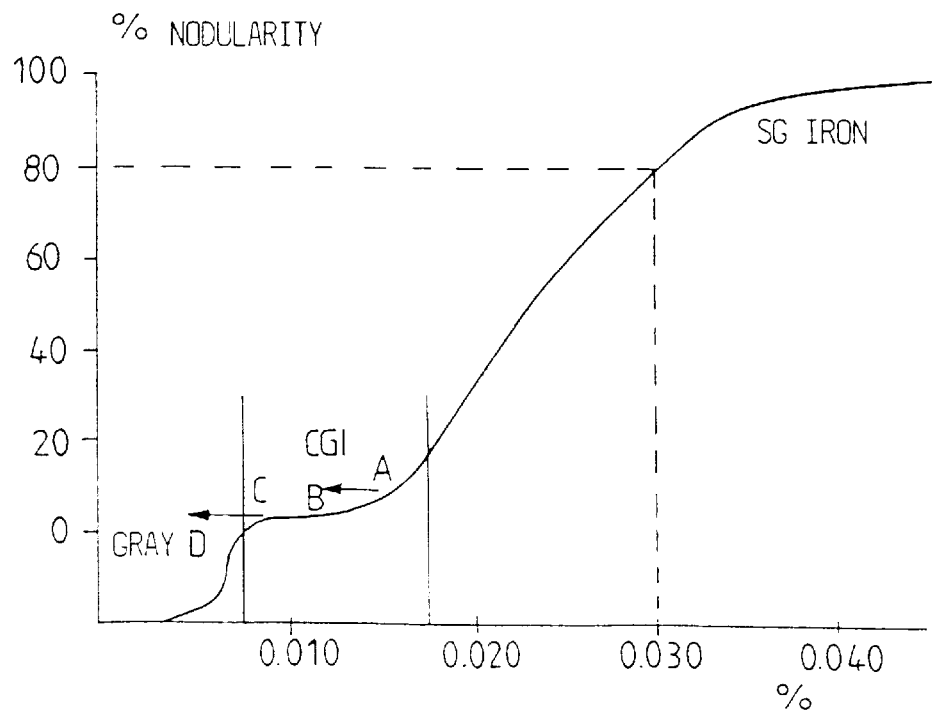

As already mentioned FIG. 2 shows the amount of spheroidal graphite iron (SGI) and grey cast iron, respectively, as a function of the magnesium level (structural modifier). If the melt composition is at point A, the wall reduction of 0.003% Mg as taught in WO92/06809 results in the near-wall melt attaining composition B which is still in the CGI plateau and therefore there is no deflection in the wall curve (as in FIG. 1). However, if the initial melt composition is at point C, the same wall reduction of 0.003% Mg results in the formation of flake iron (Point D) in the near-wall region.

It has turned out that all the measurement points referred to in WO86/01755 and WO92/06809 are essential information points. One of the data points referred to in WO86/01755 is the minimum temperature on the wall curve prior to eutectic recalescence, so-called $T_v$. However, in the presence of a wall reaction due to flake graphite formation, the minimum temperature on the wall curve is altered or "masked" by the latent heat liberated during flake formation.

Figure 3:
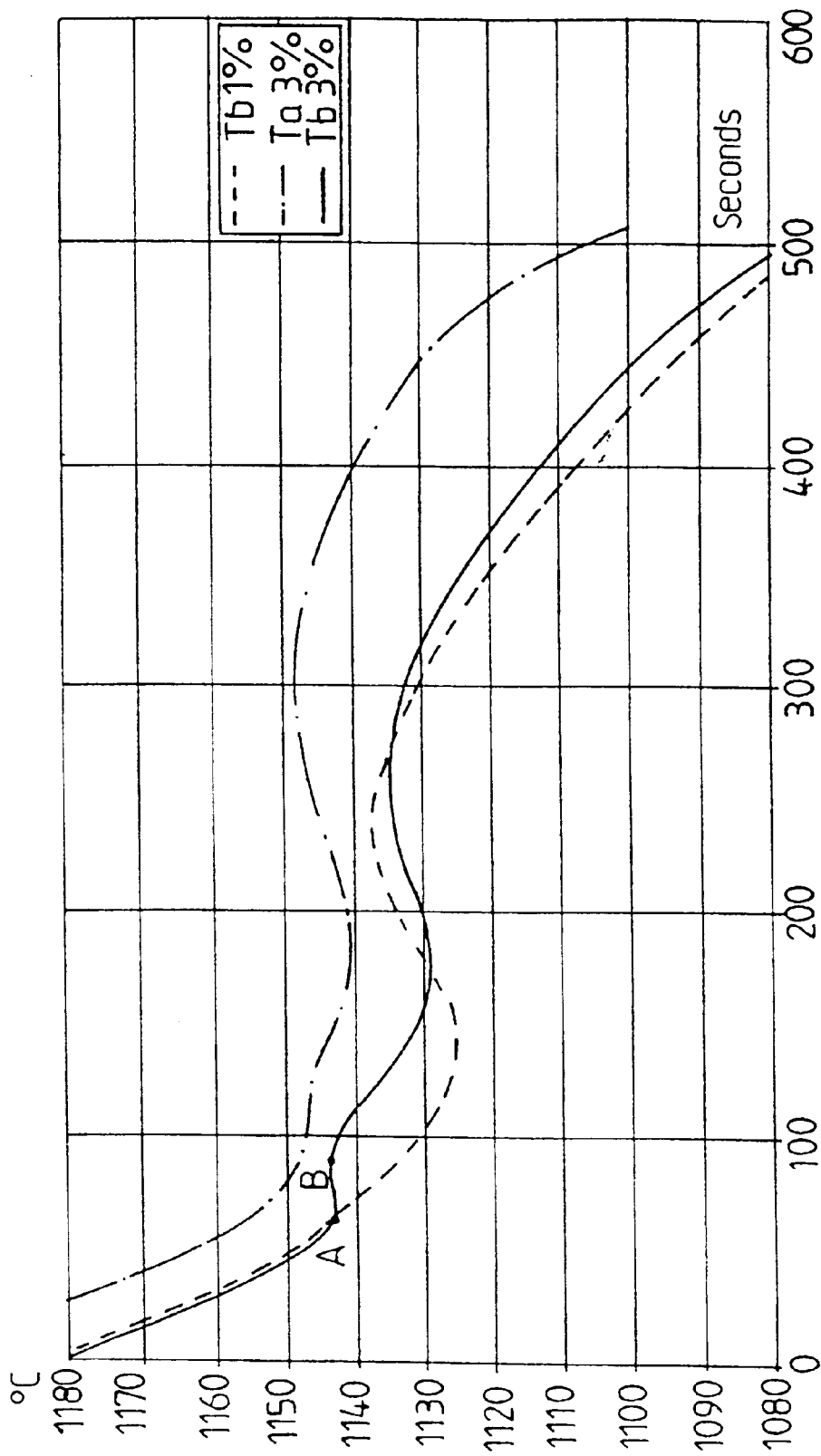
FIG. 3 shows cooling curves obtained by the present invention.

FIG. 3 illustrates an example of three cooling curves measured simultaneously under controlled conditions, from the same sample of molten compacted graphite iron (CGI) with and without wall reaction. In order to ensure a wall reaction as described in WO92/06809, one sample cup was coated with a 3% sulfur solution while the other sample cup was coated with a less reactive coating. The three cooling curves are described in more detail, according to labelling on FIG. 4b, as follows:

Ta 3% Center thermocouple from sample cup containing 3% sulfur wall coating.

Tb 3% Wall thermocouple from sample cup containing 3% sulfur wall coating.

Tb 1% Wall thermocouple from sample cup containing 1% sulfur wall coating.

FIG. 3 clearly shows a normal centre thermocouple cooling curve and two different wall cooling curves. The wall thermocouple adjacent to the 3% sulfur coating has a typically obvious wall reaction initiating at the point A (approx. 60 seconds, 1143° C.) and continuing to point B (approx. 100 seconds, 1144° C.). The ultimate result of this "shift" in the curve is that the minimum temperature on the wall curve is approximately 2.5° C. higher in the presence of a wall reaction. This is extremely important from a production point-of-view since a difference of 2.5° C. in measured undercooling can correspond to the need for +/−0.5 kg inoculant per tonne to avoid either excessive nodularity (−0.5 kg/tonne) or carbide formation (+0.5 kg/tonne) according to WO86/01755.

The use of three thermoresponsive means in the above mentioned manner provides an unforeseen advantage. Firstly, the present invention allows two distinctly different types of information to be collected. WO 86/01755 teaches the importance of simultaneously controlling the magnesium and inoculant content of the molten iron to remain within the CGI specification window. The present invention not only allows accurate measurement of both values (inoculant efficiency and proximity to grey iron) but it also allows for the coating to be extremely reactive (containing sulfur rather than reducible oxides as in WO 92/06809) without compromising the ability to measure the inoculating efficiency. This, for example, when casting components with a long pouring (small castings) or a long solidification time (large castings) allows a highly reactive coating to be used to simulate the Mg-fading, which was previously not possible in the method according to WO 92/06809 due to the adverse affect on the measurement of nucleating potential.

Figure 4:
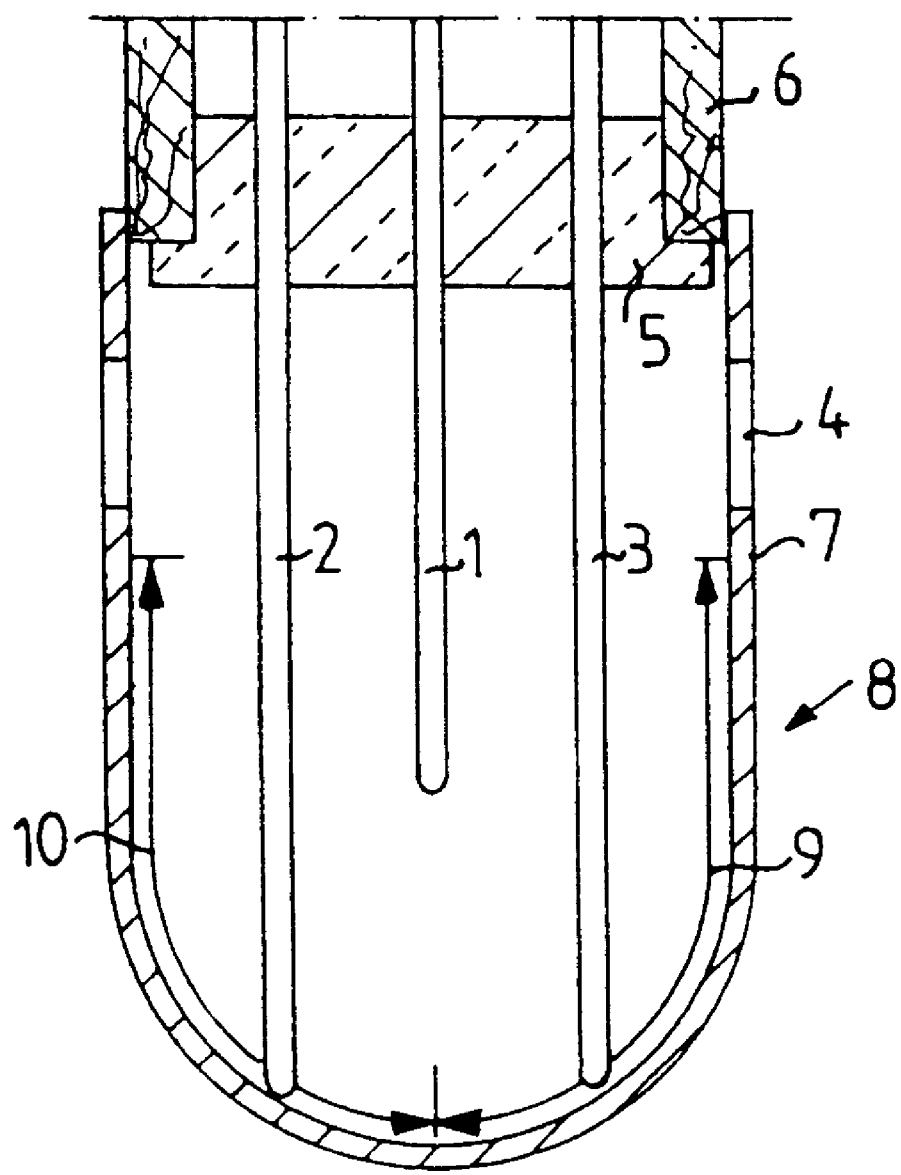
FIG. 4 is a cross section of a sample vessel equipped with three thermocouples that can be used in the method according to the present invention.

FIG. 4 discloses a sample vessel that can be used in the method according to the invention. The inner wall of a crucible (8) is partially coated with I a reactive coating (10) containing 0–5% sulfur, 0–10% of oxides of silicon, manganese or iron, or 0–0.5% of oxides of potassium and sodium; and II an relatively inert coating (9) such as aluminium or zirconium oxide.

Three thermocouples (1,2,3) arranged in such a way that one (1) is situated in the center of the crucible (8), one (2) close to the reactive coating (2) and the last one (3) close to the relatively inert coating (9), are fixed in a ceramic plug (5) and contained inside a cardboard tube (6).

What is claimed is:

1. A method of controlling a composition of a cast iron melt comprising:

preparing a cast iron melt;

adding a structure modifying agent and a nucleating agent in amounts selected to produce a fully compacted graphite iron upon solidification of the melt;

extracting a sample of the melt in a sample vessel, the sample vessel comprising:

an inner wall having an active portion and an inert portion, the active portion comprising a material which will lower a concentration of dissolved structure modifying agent in the melt by at least 0.003%;

providing at least three temperature measuring devices, at least one of the temperature measuring devices disposed substantially at a center of the sample vessel, at least one of the temperature measuring devices disposed adjacent to the active portion of the sample vessel, at least one of the temperature measuring devices disposed adjacent to the inert portion of the sample vessel;

allowing the temperature measuring devices to reach thermal equilibrium with the melt;

recording temperatures measured by the temperature measuring devices;

comparing the recorded temperatures with known cooling curves to determine any corrections to the melt, wherein the corrections are selected from the group consisting of: (a) adjusting a content of the nucleating agent and (b) adjusting a content of the structure modifying agent; and making the corrections to the composition of the melt necessary to produce compacted graphite crystals upon solidification of the melt.

2. A method according to claim 1, wherein the structure modifying agent is magnesium.

3. A method of controlling a composition of a cast iron melt comprising:

preparing a cast iron melt;

adding a structure modifying agent and a nucleating agent in amounts selected to produce a fully compacted graphite iron upon solidification of the melt;

extracting a sample of the melt in two sample vessels, a first sample vessel having an inner wall having an active portion, the active portion comprising a material which will lower a concentration of dissolved modifying agent in the melt by at least 0.003%, a second sample vessel having an inner wall having an inert portion;

providing at least three temperature measuring devices, at least one of the temperature measuring devices disposed substantially at a center of one of the sample vessels, at least one of the temperature measuring devices disposed adjacent to the active portion of the first sample vessel, at least one of the temperature measuring devices disposed adjacent to the inert portion of the second sample vessel;

allowing the temperature measuring devices to reach thermal equilibrium with the melt;

recording temperatures measured by the temperature measuring devices;

comparing the recorded temperatures with known cooling curves to determine any corrections to the melt, wherein the corrections are selected from the group consisting of: (a) adjusting a content of the nucleating agent and (b) adjusting a content of the structure modifying agent; and making the corrections to the composition of the melt necessary to produce compacted graphite crystals upon solidification of the melt.

4. A method according to claim 3, wherein the structure modifying agent is magnesium.

5. A method according to claim 1, wherein the active portion of the inner wall of the sample vessel comprises an area of the inner wall having a coating comprising 0–5% sulfur, 0–10% of a material selected from the group consisting of silicon, manganese and iron, and 0–0.5% oxides of potassium and sodium.

6. A method according to claim 3, wherein the active portion of the inner wall of the first sample vessel comprises an area of the inner wall having a coating comprising 0–5% sulfur, 0–10% of a material selected from the group consisting of silicon, manganese and iron, and 0–0.5% oxides of potassium and sodium.

7. A method according to claim 2, wherein the active portion of the inner wall of the sample vessel comprises an area of the inner wall having a coating comprising 0–5% sulfur, 0–10% of a material selected from the group consisting of silicon, manganese and iron, and 0–0.5% oxides of potassium and sodium.

8. A method according to claim 4, wherein the active portion of the inner wall of the first sample vessel comprises an area of the inner wall having a coating comprising 0–5% sulfur, 0–10% of a material selected from the group consisting of silicon, manganese and iron, and 0–0.5% oxides of potassium and sodium.

9. A method according to claim 7, wherein the coating comprises 3–5% sulfur.

10. A method according to claim 8, wherein the coating comprises 3–5% sulfur.

11. A method according to claim 1, wherein the temperature measuring devices comprise thermocouples.

12. A method according to claim 3, wherein the temperature measuring devices comprise thermocouples.

13. A method according to claim 1, wherein the temperature measuring devices comprise pyrometric devices.

14. A method according to claim 3, wherein the temperature measuring devices comprise pyrometric devices.

* * * * *